United States Patent
Doris et al.

(10) Patent No.: US 12,181,470 B2
(45) Date of Patent: Dec. 31, 2024

(54) REGENERABLE AFFINITY SENSORS AND ASSOCIATED METHODS

(71) Applicant: Palo Alto Research Center Incorporated, Palo Alto, CA (US)

(72) Inventors: Sean Doris, San Francisco, CA (US); Anne Plochowietz, Mountain View, CA (US); Jerome Unidad, San Francisco, CA (US)

(73) Assignee: Xerox Corporation, Norwalk, CT (US)

( * ) Notice: Subject to any disclaimer, the term of this patent is extended or adjusted under 35 U.S.C. 154(b) by 477 days.

(21) Appl. No.: 17/481,806

(22) Filed: Sep. 22, 2021

(65) Prior Publication Data
US 2023/0097591 A1   Mar. 30, 2023

(51) Int. Cl.
*G01N 33/543* (2006.01)
(52) U.S. Cl.
CPC .............. *G01N 33/54373* (2013.01)
(58) Field of Classification Search
CPC .............. G01N 33/54373; G01N 33/84; G01N 33/5302; G01N 33/543; G01N 33/5433; G01N 33/5438; G01N 33/551; G01N 27/302; G01N 27/327; G01N 27/3275; G01N 27/301; G01N 27/3276
USPC ........... 435/7.1, 6.1, 4, 287.1; 436/501, 518; 204/400, 403.01, 416, 433; 422/82.01, 422/82.03
See application file for complete search history.

(56) References Cited

U.S. PATENT DOCUMENTS

| | | |
|---|---|---|
| 9,075,041 B2 | 7/2015 | Kavusi et al. |
| 9,188,585 B2 | 11/2015 | Kavusi et al. |
| 9,810,688 B2 | 11/2017 | Fomina et al. |
| 9,874,538 B2 | 1/2018 | Johnson et al. |
| 10,011,549 B2 | 7/2018 | Johnson et al. |
| 10,041,905 B2 | 8/2018 | Johnson et al. |
| 10,379,080 B2 | 8/2019 | Johnson et al. |
| 2019/0018004 A1* | 1/2019 | Shin ............ G01N 33/5375 |

FOREIGN PATENT DOCUMENTS

WO   2019160932   8/2019

OTHER PUBLICATIONS

Reverberi R, Reverberi L. Factors affecting the antigen-antibody reaction. Blood Transfus. Nov. 2007;5(4):227-40. doi: 10.2450/2007.0047-07. (Year: 2007).*

(Continued)

*Primary Examiner* — Christopher L Chin
*Assistant Examiner* — Christina Lusi
(74) *Attorney, Agent, or Firm* — Vorys, Sater, Seymour and Pease LLP

(57) ABSTRACT

Affinity sensors may exhibit advantaged regeneration behavior when pH is changed in proximity to a sensing element. Such affinity sensors may comprise at least one sensing element comprising a recognition moiety that interacts with an analyte by reversibly forming an analyte complex, and a solid-state pH-modulating element in proximity to the at least one sensing element, wherein formation of the analyte complex is pH-dependent and the at least one sensing element provides a signal that changes when the analyte complex reversibly forms, and a change in magnitude of the signal is correlatable to an amount of analyte interacted with the at least one sensing element.

21 Claims, 3 Drawing Sheets

(56) References Cited

OTHER PUBLICATIONS

Frasconi M, Tel-Vered R, Elbaz J, Willner I. Electrochemically stimulated pH changes: a route to control chemical reactivity. J Am Chem Soc. Feb. 17, 2010;132(6):2029-36. (Year: 2010).*
Brody, E.N., et al., "High-content affinity-based proteomics: Unlocking protein biomarker discovery," Expert Rev. Mol. Diagn., 2010, pp. 1013-1022, 10.
Goode, J.A., et al., "Biosensor Regeneration: A Review of Common Techniques and Outcomes," Langmuir, 2015, pp. 6267-6276, 31.
Belleperche, M., et al., "pH-control in aptamer-based diagnostics, therapeutics, and analytical applications," Pharmaceuticals, 2018, 13 pp., 1.
Strakosas, X., et al., "A Bioelectronic Platform Modulates pH in Biologically Relevant Conditions," Adv. Sci., 2019, pp. 1-7, 6.
Kopera, J.J.C., "Inside the Nickel Metal Hydride Battery," https://www.cobasys.com/pdf/tutorial/InsideNimhBattery/inside_nimh_battery_technology.html, 2004, downloaded Sep. 9, 2021.
Wang, G., et al., "A review of electrode materials for electrochemical supercapacitors," Chem. Soc. Rev., 2012, pp. 797-828, 41.
Zdrachek, E., et al., "Potentiometric Sensing," Anal. Chem., 2019, pp. 2-26, 91.

* cited by examiner

REGENERABLE AFFINITY SENSORS AND ASSOCIATED METHODS

BACKGROUND

Sensors may be utilized to monitor a broad range of analytes. In performing analyte monitoring, sensors may selectively detect a particular analyte or a range of related analytes having similar properties. Depending upon the operational principles employed, a given sensor may promote analyte detection through an optical response, a coulometric response, an electrochemical response detectable voltametrically or amperometrically, a thermal response, a gravimetric response, a calorimetric response, or any combination thereof.

One class of sensors may employ a recognition moiety to facilitate selective detection of a particular analyte or a group of structurally related analytes. The recognition moiety may exhibit binding affinity for forming an analyte complex when interacted with the analyte, such that the analyte complex is analytically detectable. Such sensors may be referred to as "affinity sensors" by virtue of their formation of the analyte complex. The recognition moiety may be biological in origin, due to the high binding selectivity frequently exhibited by biological molecules, in which case the sensors may be referred to by the more specific term "affinity biosensors." Biomimetic or bio-inspired recognition moieties may likewise exhibit high binding selectivity toward particular analytes. Provided that they can be constructed to provide sufficient recognition and binding selectivity, synthetic recognition moieties (e.g., crown ethers, calixarenes, and similar host-guest supramolecular entities) may be utilized in affinity sensors as well. As such, depending on the type of recognition moiety employed, suitable analytes that may be analyzed with an affinity sensor may be biological or non-biological in nature.

Complex formation in an affinity sensor may be defined by the equilibrium reaction shown in Reaction 1, Reaction 1

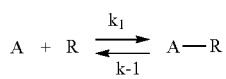

wherein A is an analyte, R is a recognition moiety, $k_1$ is the forward rate constant, and $k_{-1}$ is the reverse rate constant, and A-R is a complex formed between the analyte and the recognition moiety. The overall equilibrium constant, K, is defined by $k_1/k_{-1}$. In order for an affinity sensor to have adequate accuracy and sensitivity for detecting low concentrations of analyte A, the overall equilibrium constant is desirably as large as possible to promote conversion of substantially all of analyte A into complex A-R for analytical detection thereof. That is, the equilibrium position of Reaction 1 is desirably shifted in the forward direction as much as possible. A large value of the overall equilibrium constant K may be attained in most cases by selecting a recognition moiety R that exhibits a low reverse rate constant $k_{-1}$ for binding analyte A.

A difficulty associated with affinity sensors, particularly when the forward rate constant $k_1$ is significantly greater than the reverse rate constant $k_{-1}$, is that the analytical recovery time may be exceedingly slow, since analyte A remains bound to recognition moiety R in the form of a complex and continues to provide an analytical signal. The affinity sensor may eventually become saturated with analyte A and no longer produce a signal indicative of a change in concentration of analyte A. If an affinity sensor is being utilized to monitor the concentration of analyte A in real-time, for instance, a decreased concentration of analyte A may not be observed, since a significant amount of complex A-R may remain in, on or otherwise associated with the affinity sensor and provide an analytical signal higher in magnitude than is truly indicative of the current quantity of analyte A. In the extreme case, it may be difficult to decomplex analyte A from the affinity sensor such that subsequent measurements of samples containing analyte A may be made. If analyte A cannot be effectively decomplexed from the recognition element, the affinity sensor may effectively become a single-use item, which may be undesirable due to cost of materials and excessive waste generation. As a consequence of the difficulties associated with slow regeneration, affinity sensors may trade sensitivity (by selecting a recognition moiety R having a lower overall equilibrium constant K for analyte A, by way of a larger reverse rate constant $k_{-1}$) so that a decreased regeneration time may be realized.

One strategy for addressing slow sensor regeneration is to alter the conditions to which complex A-R is exposed. Conditions such as pH, ionic strength, heat, decomplexing agents, or other stimuli may break complex A-R and shift the reaction equilibrium back toward free analyte A, thereby regenerating the affinity sensor for making subsequent measurements. However, application of the foregoing stimuli and others may undesirably alter a sample containing analyte A. For example, reagents added to a sample to promote shifting of the reaction equilibrium may be especially undesirable when label-free, continuous sensing is desired. Added reagents or other stimuli may also further alter a sample and hamper accurate measurement of an analyte concentration therein. Further, when a process stream is being analyzed, added reagents may undesirably alter the process stream and potentially render it unsuitable for its intended purpose.

SUMMARY

In some embodiments, the present disclosure provides affinity sensors comprising: at least one sensing element comprising a recognition moiety that interacts with an analyte by reversibly forming an analyte complex; and a solid-state pH-modulating element in proximity to the at least one sensing element. Formation of the analyte complex is pH-dependent, and the at least one sensing element provides a signal that changes when the analyte complex reversibly forms, and a change in magnitude of the signal is correlatable to an amount of analyte interacted with the at least one sensing element.

In some embodiments, the present disclosure provides sensing methods comprising: interacting an analyte with a sensing element comprising a recognition moiety that reversibly forms an analyte complex in a pH-dependent manner, the sensing element changing from a first state to a second state upon interacting with the analyte to form the analyte complex; and actuating a solid-state pH-modulating element positioned in proximity to the sensing element. The sensing element provides a signal that changes when the analyte complex reversibly forms, and a change in magnitude of the signal between the first state and the second state is correlatable to an amount of analyte interacted with the sensing element;

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
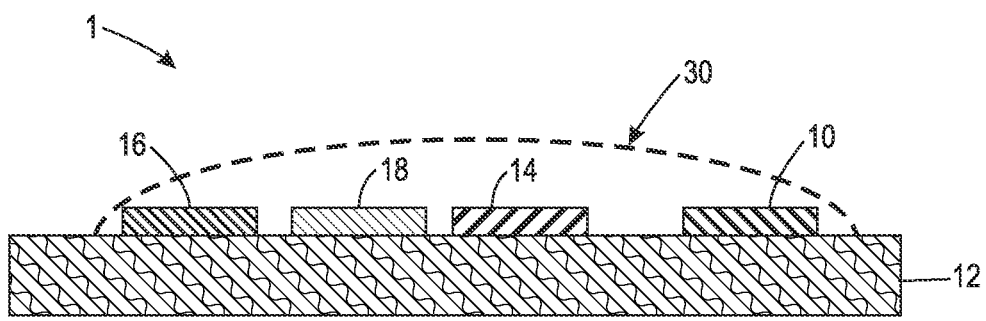
FIG. 1 shows a diagram of an affinity sensor having a solid-state pH-modulating element in proximity to and horizontally spaced apart from a sensing element, according to one or more embodiments of the present disclosure.

The present disclosure generally describes sensors and sensing methods for monitoring one or more analytes and, more specifically, affinity sensors and associated methods that may be regulated through pH adjustment.

As discussed above, affinity sensors may afford good selectivity toward assaying various analytes within a sample. However, if the reverse rate constant of an affinity sensor is excessively small, the slow reverse reaction rate may cause the affinity sensor to undergo correspondingly slow regeneration to restore detection sensitivity. A false-positive analyte signal may otherwise result. In the extreme case, it may not be possible to regenerate an affinity sensor, effectively making the affinity sensor suitable for only a single use. As such, slow or negligible sensor regeneration may be exceedingly problematic. Various stimuli may be applied to shift the equilibrium position of a reaction forming an analyte complex bound to an affinity sensor, but added reagents or other conditions used in shifting the equilibrium may undesirably change the characteristics of a sample being assayed.

The present disclosure describes affinity sensors that may be regenerated through locally altering pH in proximity to a sensing element capable of forming an analyte complex. By altering the pH to which a sensing element is exposed, the recognition moiety associated with the sensing element and/or the analyte itself may experience one or more changes, which may alter the rate at which the recognition moiety releases an analyte bound in an analyte complex. For example, an analyte, a recognition element, or an analyte complex exposed to an altered pH environment may undergo protonation or deprotonation, which may alter charge, polarity, conformation, or any combination thereof. The altered charge, polarity, and/or conformation of the analyte, the recognition element, and/or the analyte complex may impact the rate of analyte release from an analyte complex. In another example, locally altering the pH may induce denaturation or a significant change in conformation/folded structure of protein or similar analytes, protein recognition elements, and/or protein analyte complexes as a result of the pH change. Similar effects may occur for nucleic acid analytes, nucleic acid recognition elements (e.g., aptamers), or nucleic acid analyte complexes, as well as protein-nucleic acid complexes. Where the structural changes are drastic (e.g., switching of a globular protein into a more extended conformation or destabilization of a DNA/RNA secondary structure having a target binding pocket), the rate of analyte release from the analyte complex may be impacted. By tailoring pH to promote analyte release in any of the foregoing manners, the reverse rate constant may be made larger than before pH modification takes place, thereby facilitating sensor regeneration.

Unlike prior affinity sensors employing external pH modification (e.g., through addition of one or more reagents) to promote sensor regeneration, the affinity sensors disclosed herein may alter pH locally in close proximity to a recognition moiety associated with a sensing element. Alternation of the pH in close proximity to a recognition moiety may promote analyte decomplexation while avoiding a change in the bulk properties of a sample through reagent addition. More particularly, the present disclosure provides affinity sensors in which a solid-state pH-modulating element is locating in proximity to a sensing element, wherein the solid-state pH-modulating element is operative to promote a pH change by oxidation or reduction of a solid material associated with the solid-state pH-modulating element. As such, the solid-state pH-modulating element may promote a pH change locally about the solid-state pH-modifying element and the sensing element without releasing or withdrawing protons or other chemical species into the entirety of a sample. In non-limiting embodiments, the solid-state pH-modulating element may be electrochemical in nature, such that application of a potential or current thereto releases protons into or withdraws protons from a sample, such that the change in local pH about the sensing element may promote analyte decomplexation from the affinity sensor. Other prior approaches for modulating pH within a sample to promote analyte decomplexation, such as electrolysis of water or enzyme binding to an affinity sensor surface, have related limitations that may be overcome in the affinity sensors disclosed herein.

Other advantages may also be realized with the affinity sensors of the present disclosure as well. For example, the affinity sensors of the present disclosure also may preclude having to maintain a reservoir (supply) of pH-modifying reagent (acid, base, and/or a precursor to an acid or a base, including electrochemically active species that promote a pH change when altering their oxidation state) and monitoring addition of the pH-modifying reagent to a sample, thereby lowering capital equipment and consumables expenses, and improving analytical simplicity. Further, in addition to promoting analyte decomplexation from an affinity sensor, the solid-state pH-modulating element may alternately be utilized to alter pH to promote analyte binding to an affinity sensor instead. In another example, the solid-state pH-modulating element may be utilized to alter pH in proximity to a sensing element to promote binding of one analyte over another, promote binding of an analyte in preference to an interferent, or any combination thereof.

Accordingly, affinity sensors of the present disclosure may comprise at least one sensing element comprising a recognition moiety that interacts with an analyte by reversibly forming an analyte complex, and a solid-state pH-modulating element in proximity to the at least one sensing element. According to the present disclosure, formation of the analyte complex is pH-dependent, and the at least one sensing element provides a signal that changes when the analyte complex reversibly forms. A change in magnitude of the signal is correlatable to an amount of analyte interacted with the at least one sensing element. Further details are provided hereinafter.

An analyte complex whose formation is "pH-dependent" means that formation of the analyte complex occurs more readily at certain pH values relative to other pH values. In particular examples, the analyte complex may form over a first range of pH values and break apart over a second range of pH values. The first range of pH values may differ from the second range of pH values by at least about 0.5 pH units, or at least about 1 pH unit, or at least about 1.5 pH units, or at least about 2 pH units, or at least about 2.5 pH units, or at least about 3 pH units, or at least about 3.5 pH units, or at least about 4 pH units, or at least about 4.5 pH units, or at least about 5 pH units, or at least about 5.5 pH units, or at least about 6 pH units, or at least about 6.5 pH units, or at least about 7 pH units.

The at least one sensing element and the solid-state pH-modulating element may be located in proximity to one another upon an in-common (single) substrate. Alternately, the at least one sensing element and the solid-state pH-modulating element may be located upon separate substrates that are placed in proximity to one another to accomplish similar benefits to those realized when the at least one sensing element and the solid-state pH-modulating element are located on an in-common substrate. In being placed in proximity to one another, the at least one sensing element and the solid-state pH-modulating element are spaced apart from one another to at least some degree. The separation between the at least one sensing element and the solid-state pH-modulating element may be selected such that the solid-state pH-modulating element, when actuated, is effective to promote analyte decomplexation from the at least one sensing element. In non-limiting examples, the separation between the at least one sensing element and the solid-state pH-modulating element may be about 10 mm or less, or about 5 mm or less, or about 4 mm or less, or about 3 mm or less, or about 2 mm or less, or about 1 mm or less, or about 900 microns or less, or about 800 microns or less, or about 700 microns or less, or about 600 microns or less, or about 500 microns or less, or about 400 microns or less, or about 300 microns or less, or about 200 microns or less, or about 100 microns or less. A minimum separation between the at least one sensing element and the solid-state pH-modulating element may be dictated by the chosen manufacturing process and sensor configuration, and may be at least about 10 microns, at least about 20 microns, or at least about 50 microns in particular embodiments. The minimum separation between the at least one sensing element and the solid-state pH-modulating element may be even smaller when the at least one sensing element and the solid-state pH-modulating element are stacked upon each other (e.g., see FIG. 3C). When stacked upon one another in the foregoing manner, the separation between the at least one sensing element and the solid-state pH-modulating element may be dictated by the thickness of an insulation layer in between, which may afford a separation down to about 10 nm, or down to about 20 nm, or down to about 30 nm, or down to about 50 nm. The foregoing distances represent a minimum separation between the at least one sensing element and the solid-state pH-modulating element. It is to be recognized that some portions of the at least one sensing element and the solid-state pH-modulating element may be located farther apart from one another than are others.

In various embodiments, the solid-state pH-modulating element may be electrochemical in nature and comprise a working electrode and at least one additional electrode. The at least one additional electrode may comprise a counter-reference electrode or separate counter and reference electrodes. That is, the solid-state pH-modulating element of the disclosed affinity sensors may be present in a two-electrode or three-electrode configuration. When a reference electrode is omitted, the at least one additional electrode may serve as a counter-reference electrode. The reference electrode or counter-reference electrode may comprise a portion of another electrical device, as explained hereinafter.

The at least one additional electrode (e.g., a counter electrode or counter-reference electrode) may be present in various configurations and locations in the disclosure herein. For example, the at least one additional electrode may promote oxidation or reduction of a solvent (e.g., water) or a sample component in response to a current produced during pH modulation, such as may be performed with a Pt counter electrode. To minimize risk of an oxidation or reduction product interfering with pH modulation, the at least one additional electrode may be spaced apart a sufficient distance from the solid-state pH-modulating element to significant preclude diffusion to the sensing element. Another embodiment may utilize a second solid-state pH-modulating element as the at least one additional electrode. By utilizing a second solid-state pH-modulating element as the at least one additional electrode, any pH changes produced at a first solid-state pH-modulating element may be reversed to avoid a global pH change in a sample (e.g., in a flow-through sensor, where pH adjustment for analyte measurement may be desirable, a first solid-state pH-modulating element may modify pH initially to promote analyte detection, and a second solid-state pH-modulating element may reverse the pH change immediately before the analyzed sample is discharged back to bulk sample, thereby maintaining the sample pH at or near a preset level on the whole). In still other embodiments, the at least one additional electrode may comprise an electrode for a supercapacitor or similar energy storage device, thereby storing charge and avoiding oxidation or reduction reactions that may otherwise occur. By storing charge instead of promoting an electrochemical side reaction, the solid-state pH-modulating electrode and the at least one additional electrode may be located closer to one another.

FIG. 1 shows a diagram of an affinity sensor having a solid-state pH-modulating element in proximity to and spaced apart from a sensing element located upon an in-common substrate. As shown in FIG. 1, affinity sensor 1 includes sensing element 10 located upon substrate 12. Also located upon substrate 12 are working electrode 14, counter electrode 16, and optional reference electrode 18. If reference electrode 18 is optionally omitted, then counter electrode 16 may serve both counter electrode and reference electrode functions (i.e., as a counter-reference electrode). Working electrode 14 may be positioned closer to sensing element 10 upon substrate 12 than is counter electrode 16. Although shown in FIG. 1 as being spaced apart from one another upon the surface of substrate 12, one or more of sensing element 10, working electrode 14, counter electrode 16, and optional reference electrode 18 may be recessed below the surface of substrate 12 in alternative sensor configurations. Electrical connections to working electrode 14, counter electrode 16 and optional reference electrode 18 are not believed to be particularly limited in position and are omitted from FIG. 1 in the interest of simplicity.

Figure 2:
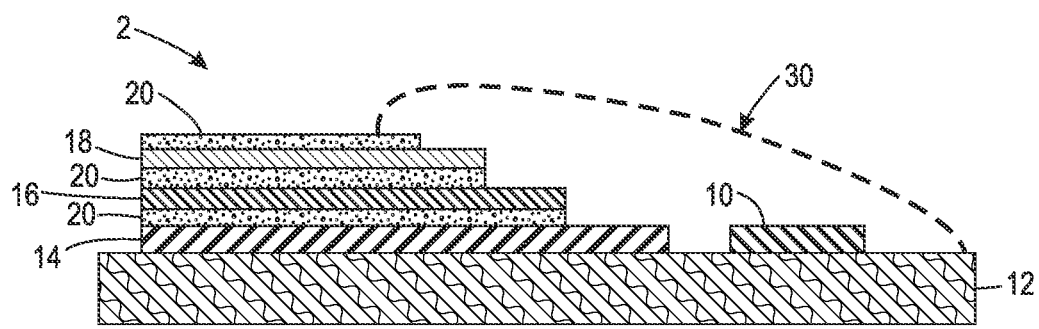
FIG. 2 shows a diagram of an affinity sensor having a stacked solid-state pH-modulating element in proximity to and spaced apart from a sensing element, according to one or more embodiments of the present disclosure.

Working electrode 14, counter electrode 16 and optional reference electrode 18 need not necessarily be laterally spaced apart from one another in the manner shown in FIG. 1. As shown in FIG. 2, affinity sensor 2 includes working electrode 14, counter electrode 16, and optional reference electrode 18 stacked upon each other with dielectric (insulation) layer 20 sandwiched in between each electrode layer or overcoating a portion of the top-most electrode layer. It is to be appreciated that the stacking order of working electrode 14, counter electrode 16, and optional reference electrode 18 may differ from that depicted. As with affinity sensor 1 (FIG. 1), one or more of sensing element 10, working electrode 14, counter electrode 16, and optional reference electrode 18 may similarly be recessed below the surface of substrate 12 in alternative sensor configurations. Likewise, electrical connections are not believed to be particularly limited in position and are omitted from FIG. 2 in the interest of simplicity.

When a potential or current is applied to working electrode 14 in the disclosure herein, a material therein may generate or consume protons, thereby promoting a pH change within region 30 in proximity to sensing element 10. As discussed above, an analyte bound to sensing element 10 may undergo decomplexation once a suitable change in pH has occurred within region 30. The size of region 30 may depend upon non-limiting factors such as, for example, the separation between working electrode 14 and sensing element 10, the potential or current applied to working electrode 14 and the amount of time the potential or current is applied, the particular material and amount thereof in working electrode 14, and the like.

Figure 3A:
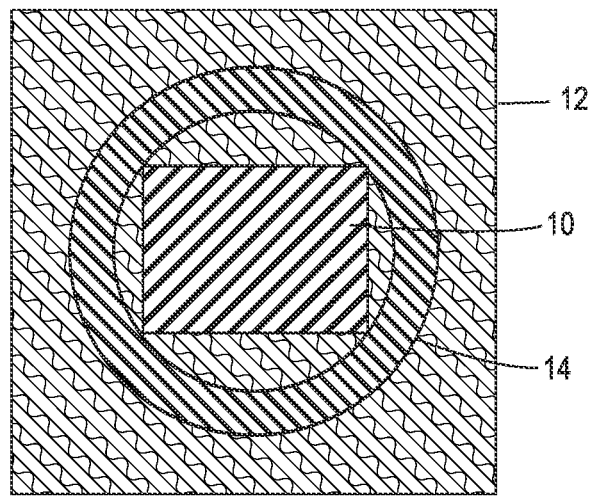
FIGS. 3A-3C show diagrams of alternative arrangements of a solid-state pH-modulating element and sensing element positioned in proximity to and spaced apart from one another, according to one or more embodiments of the present disclosure.
Figure 3B:
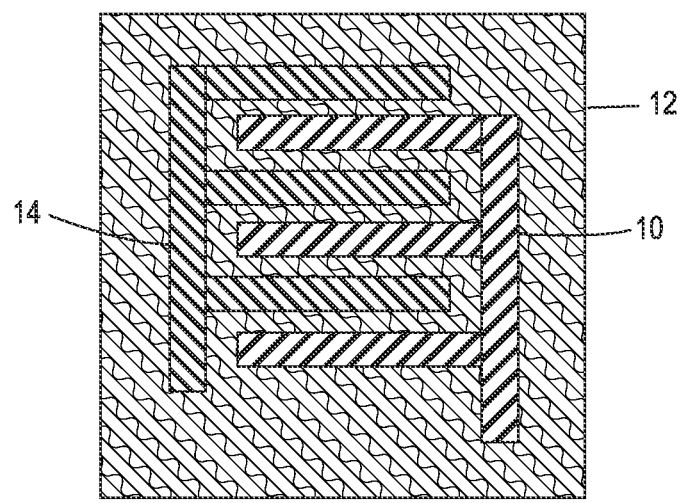
Figure 3C:
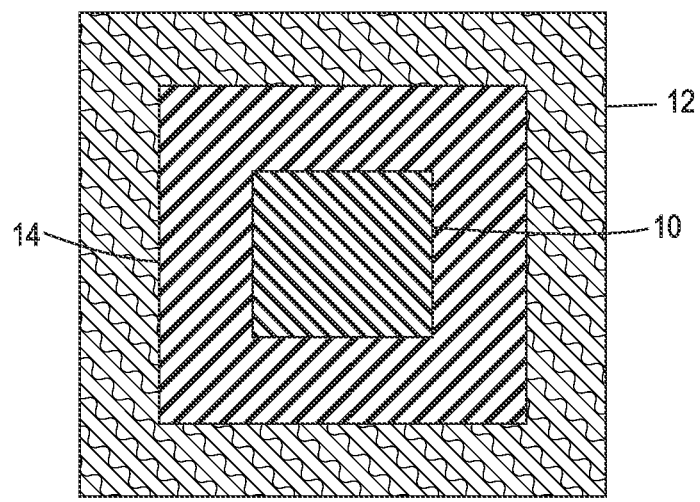

Sensing element 10 and working electrode 14 also need not necessarily be horizontally spaced apart from one another in the manner shown in FIGS. 1 and 2. FIGS. 3A-3C show illustrative alternative configurations for sensing element 10 and working electrode 14 upon substrate 12. Such alternative configurations may be utilized in any of the affinity sensors disclosed herein. In non-limiting examples, working electrode 14 may at least partially surround sensing element 10 (FIG. 3A), and/or working electrode 14 and sensing element 10 may be interdigitated with one another (FIG. 3B), and/or sensing element 10 may be stacked upon working electrode 14 (FIG. 3C). When sensing element 10 and working electrode 14 are disposed in a stacked configuration, a dielectric layer (not visible in FIG. 3C) may be utilized to provide electrical isolation therebetween. Alternative interdigitated arrangements of working electrode 14 and sensing element 10 may be curved or spiral-like in nature.

The signal produced by the at least one sensing element may be detectable through optical detection, electrochemical detection, thermal detection, gravimetric detection, calorimetric detection, or any combination thereof. Any of these detection techniques may be facilitated through reversible analyte complex formation according to the disclosure herein. Other sensor components utilized to promote analyte detection by a particular sensing technique will be familiar to one having ordinary skill in the art and are not discussed in further detail herein, except as provided further below.

In particular examples, detection of the analyte may occur electrochemically, in which case the sensing element may comprise a working electrode, a counter electrode, and an optional reference electrode, which are collectively operable to promote detection of an analyte through observation of a current or potential. The working electrode, counter electrode, and optional reference electrode associated with the at least one sensing element may be separate from the working electrode and counter electrode associated with the solid-state pH-modulating element. Alternately, the sensing element and the solid-state pH-modulating element may share a working electrode and/or counter electrode.

Regardless of how the at least one sensing element promotes signal detection, a recognition moiety may be present that promotes reversible complex formation with an analyte of interest. The recognition moiety may be a bio-based moiety or biomimetic moiety in particular embodiments. Suitable bio-based and biomimetic recognition moieties that may promote formation of an analyte complex in the disclosure herein include, but are not limited to, an antibody, a protein, a polypeptide, an aptamer (including DNA and/or RNA aptamers), an affimer, a molecularly imprinted polymer, a glycopolymer, an oligonucleotide, and any combination thereof. Particular bio-based and biomimetic recognition moieties may be selected based upon the analyte of interest to be analyzed. Synthetic recognition moieties that are not bio-inspired may also be suitable for use in the disclosure herein, provided that such recognition moieties have sufficient binding selectivity.

As discussed above, the solid-state pH-modulating element may comprise a working electrode and at least one additional electrode, wherein a material operable to generate or consume protons upon undergoing oxidation or reduction is associated with the working electrode of the solid-state pH-modulating element. Upon applying a potential or current to the working electrode, the material may undergo oxidation or reduction to generate or consume protons, thereby altering pH in a region proximate to the working electrode and the sensing element. Suitable materials for generating or consuming protons upon application of a potential or current thereto may include, but are not limited to, metal hydrides, metal oxides (e.g., NiO(OH), $IrO_2$, ZnO, $WO_3$, $RuO_2$, $Co_3O_4$, and the like), metal hydroxides (e.g., $Co(OH)_2$ and the like), polyaniline, quinone-containing polymers, and any combination thereof. More specific examples of suitable materials for generating or consuming protons are provided below.

In one example, the solid-state pH-modulating element may comprise a Pd/PdH working electrode, which generates or consumes protons by the reversible electrochemical process shown in Reaction 2. It is to be appreciated that the entirety of the working electrode need not necessarily be formed from Pd.

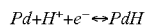

Reaction 2

As shown, a Pd/PdH working electrode may consume protons through reduction and generate protons through oxidation, thereby increasing or decreasing the pH, respectively, in proximity to the at least one sensing element. Other suitable examples of metal hydrides that may generate or consume protons through oxidation or reduction include, but are not limited to, complex metal hydrides having a formula of $A_xB_yH$, wherein A and B are metals, x is 1 or 2, and y is 1, 2 or 5. Some examples of suitable complex metal hydrides are shown in Table 1 below.

TABLE 1

| Complex Metal Hydride | A= | B= |
|---|---|---|
| $AB_5H$ | Rare-earth alloy (mischmetal), La, Ce, or Ti | Ni, Co, Mn, or Al |
| $AB_2H$ | V or Ti | Zr in combination with Cr, Co, Fe, or Mn |
| ABH | Zr or Ti | Ni, Fe, Cr, or V |
| $A_2BH$ | Mg or Ti | Ni |

The optional reference electrode, if present, may be a Ag/AgCl electrode or a saturated calomel electrode, in non-limiting examples. Other suitable reference electrode materials will be familiar to one having ordinary skill in the art and may be employed in any of the affinity sensors disclosed herein.

The counter electrode of the solid-state pH-modulating element may comprise any material that is capable of accepting or releasing charge as the working electrode is oxidized or reduced. Suitable materials for the counter electrode may include, but are not limited to, platinum, gold, carbon, PEDOT:PSS, Prussian blue, or the like. Optionally, the counter electrode may also be capable of producing or consuming protons. When the counter electrode is capable of producing or consuming protons, the counter electrode and working electrode may be separated from each other by a suitable distance such that the pH change promoted by the solid-state pH-modulating element is not appreciably negated. For example, in such instances, the counter electrode and working electrode may be separated by at least about 1 mm up to about 5 mm, or up to about 10 mm, or up to about 20 mm, or even a greater separation. Additional disclosure regarding the counter electrode and positioning thereof is provided above.

In instances where it is undesirable for the counter electrode to change the composition or pH of a sample on the whole, the counter electrode may be incorporated within a supercapacitor or other charge storage device. For example, in these cases, the counter electrode may comprise a high surface area material such as carbon (e.g., carbon black, activated carbon, graphene, single-walled carbon nanotubes, multi-walled carbon nanotubes, carbon fiber, or the like), a conductive polymer (e.g., polyaniline, PEDOT:PSS, polypyrrole, polythiophene, or the like), a redox-active polymer, a metal oxide (e.g., $RuO_2$, $SnO_2$, $MnO_2$, NiO, $TiO_2$, or the like), or any combination thereof, any of which may promote charge storage in an electrochemical double-layer or at internal redox sites (pseudocapacitive storage).

A difference in the signal magnitude before and after exposing the sensing element to the analyte (difference signal) may allow a concentration of the analyte to be determined. The difference signal may be correlated to an analyte concentration by consulting a lookup table, calibration curve, or the like. Optionally, the affinity sensors of the present disclosure may further comprise a processor configured to determine a concentration of the analyte based upon the change in magnitude of the signal.

Similarly, when regenerating the affinity sensor by actuating the working electrode to promote analyte decomplexation, the magnitude of the signal may be followed until the signal magnitude stabilizes or the rate of change of the signal becomes acceptably low, either of which may be indicative of analyte decomplexation. It should be appreciated that the entirety of the analyte may not undergo decomplexation in some instances. Provided that at least some of the analyte undergoes decomplexation from the sensing element and the activity of the sensing element is at least partially restored, the features of the present disclosure may be met. Once a sufficient amount of decomplexation has taken place, further measurements of the analyte may be conducted. Like determination of the analyte concentration, a processor may be employed to actuate the solid-state pH-modulating element and follow the analyte decomplexation for a specified length of time.

Various aspects of the present disclosure may utilize computer systems, such as to process data received from the affinity sensors disclosed herein. Systems and methods utilizing the affinity sensors may include a non-transitory computer readable medium containing instructions that, when implemented, cause one or more processors to carry out one or more aspects described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present disclosure may be considered to include a tangible storage medium or tangible distribution medium and art-recognized equivalents and successor media, in which software implementations of the present disclosure are stored.

The present disclosure may be implemented using computing devices or processor-based devices that include a processor; a memory coupled to the processor; and instructions provided to the memory, wherein the instructions are executable by the processor to perform one or more features of the present disclosure. The instructions can be a portion of code on a non-transitory computer readable medium. Any suitable processor-based device may be utilized for implementing all or a portion of embodiments of the present disclosure, including without limitation personal computers, networks of personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

A pH sensor may be utilized in combination with the affinity sensors disclosed herein to monitor pH as analyte decomplexation is taking place. Once a desired extent of pH adjustment has taken place, additional analyte monitoring may take place. Embodiments employing a processor for automated or semi-automated process control may access the pH sensor and actuate the solid-state pH-modulating element to achieve a desired pH setpoint.

In some embodiments, the potential measured between the working electrode of the solid-state pH-modulator and a reference electrode may be utilized for in situ pH monitoring without an additional pH sensor being present. The reaction occurring in the pH modulator is shown in Reaction 3, where A represents one or more species that comprise the solid-state pH modulator working electrode and A-H indicates the same species after uptake of a proton.

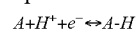

Reaction 3

The potential of the solid-state pH modulator at the working electrode with respect to the reference electrode is given by the Nernst equation (Equation 1)

$$E = E^0 - \frac{RT}{nF}\ln(Q) \qquad \text{Equation 1}$$

where E is the electrode potential, $E^0$ is standard potential for the reaction occurring at the working electrode, R is the universal gas constant, T is the temperature, n is the number of electrons transferred in the reaction, F is Faraday's constant, and Q is the reaction quotient. Since the concentration of protons is present in Q (due to protons participating in the reaction), the electrode potential is a function of pH. Accordingly, the pH may be determined based upon a calibration curve or lookup table obtained from measurement of samples having known pH.

Methods for analysis and regeneration of the affinity sensors disclosed herein may comprise: interacting an analyte with a sensing element comprising a recognition moiety that reversibly forms an analyte complex in a pH-dependent manner, such that the sensing element changes form a first state to a second state upon interacting with the analyte to form the analyte complex; and actuating a solid-state pH-modulating element positioned in proximity to the sensing element. As discussed above, the sensing element provides a signal that changes when the analyte complex reversibly forms, and a change in magnitude of a signal between the first state and the second state is correlatable to an amount of analyte interacted with the sensing element.

The local pH near the affinity sensor may be periodically oscillated between a regeneration pH and a measurement pH while the affinity sensor is being continuously measured. The period of oscillation may vary from about 1 s to about 1 hour and may allow full or partial regeneration of the affinity sensor to be realized.

Suitable analytes that may undergo analysis in the disclosure herein are not believed to be particularly limited, provided that a sensing element with sufficient selectivity for the analyte can be identified and the sensing element may undergo reversible analyte complex formation. In non-limiting examples, suitable analytes may include, but are not limited to, ions, cells, viruses, small molecules, proteins, polysaccharides, polypeptides, oligonucleotides, DNA, RNA, carbohydrates, biopolymers, synthetic polymers, and the like. Exemplary processes and industries in which the affinity sensors may be employed include, but are not limited to personalized medicine, healthcare, chemical manufacturing, drug manufacturing, food and beverage production, environmental monitoring, drug testing, and the like.

As discussed herein, actuating the solid-state pH-modulating element may accomplish one or more of changing pH at the sensing element and displacing analyte from the analyte complex to convert the sensing element from the second state to the first state, and/or allow the analyte complex to form when interacting the analyte with the sensing element, and/or allow the analyte complex to form in preference to an interferent forming an interferent complex with the sensing element, and/or allow the analyte complex of a first analyte complex to form in preference to the analyte complex of a second analyte. Thus, the solid-state pH-modulating element may cycle between at least a first pH state and a second pH state in promoting analyte decomplexation according to the disclosure herein. Optionally, the solid-state pH-modulating element may cycle between a plurality of pH states to accomplish additional features, such as to promote analyte binding, and/or preferential analyte binding over an interferent, and/or preferential analyte binding of a first analyte over a second analyte, in addition to promoting analyte decomplexation. In non-limiting examples, the solid-state pH-modulating element may also cycle through a range of pH states to promote sequential analyte binding and decomplexation from multiple sensing elements (e.g., in a sensor array), wherein each sensing element may bind a specified analyte under different pH conditions than does other analytes undergoing analysis. In any of the foregoing embodiments, actuating may comprise applying a suitable potential or current to a working electrode comprising the solid-state pH-modulating element.

The sensing element may comprise multiple affinity sensors in some embodiments. For example, an array of affinity sensors may be placed in proximity to each other and a single or multiple solid-state pH-modulating elements. The affinity sensors may be configured to detect different analytes, to bind one or more analytes at different binding constants, and/or to function at different pH values. The affinity sensors may be interrogated to determine one or more analyte concentrations concurrently, or some affinity sensors may be regenerating while others are being interrogated to determine one or more analyte concentrations.

A sensing system or a portion thereof incorporating the disclosure herein may be encompassed in a flow channel (e.g., in a flow-through sensor) or otherwise exposed to a moving fluid sample. For example, a flow channel may be configured to remove a volume of sample from the surroundings, flow the volume of sample past one or more solid-state pH-modulating electrodes, an affinity sensor, and a counter electrode (which may be a second solid-state pH-modulating element). The outlet of the sensing system may direct the volume of sample back into the surroundings (e.g., into bulk sample) or into a waste stream or container. The sensing system may further include other sample preparation or mixing operations to condition the sample for analysis and/or to remove interferents.

Optionally, prior to interacting the analyte with the sensing element, the methods of the present disclosure may comprise adjusting pH of a sample containing the analyte before interacting the analyte with the sensing element. Adjustment of the sample pH may be accomplished by adding one or more of an acid, base, or precursor to an acid or base to the sample under appropriate conditions. Alternately, an electrode may be utilized to alter the sample pH.

Alternately, the solid-state pH-modulating element may be utilized to adjust the pH of the sample before interacting the analyte with the sensing element under suitable conditions to form the analyte complex.

Optionally, the solid-state pH-modulating element may be recharged if it has become depleted of protons or saturated with protons. These events may occur if the local pH near the affinity sensor needs to be adjusted to a value that is significantly different from the bulk pH of a sample for an extended period of time. In other instances, the solid-state pH-modulating element may need to be recharged if is used to adjust the pH away from the bulk pH of a sample over many cycles. For example, if the bulk sample pH is 7 but a pH of 9 is required for sensor regeneration, repeated affinity sensor regeneration may eventually lead to proton saturation without a downward pH adjustment being performed at some point. Recharging the solid-state pH-modulating element may comprise adjusting the pH to a more acidic or basic value to add or remove protons as desired. In the preceding example, recharging the solid-state pH-modulating element may comprise lowering the local pH in order to remove protons from the solid-state pH-modulating element to facilitate later upward adjustment of pH. If needed (e.g., to prevent affinity sensor damage), recharging may be conducted slowly so that the change in local pH is negligible.

Methods of the present disclosure may further determine a change in magnitude of the signal between the first state and the second state or between the second state and the first state. The change in magnitude of the signal between the first state and the second state may be correlated to the amount of analyte that is interacted with the sensing element. Likewise, the change in magnitude between the second state and the first state may be utilized to determine when sufficient decomplexation of the analyte from the sensing element has taken place.

The affinity sensors of the present disclosure may communicate signals over a local or remote communication path or link, which may be wired or wireless. Any suitable electronic communication protocol may be used for wireless paths or lengths, such as near field communication (NFC), radio frequency identification (RFID), BLUETOOTH® or BLUETOOTH® Low Energy protocols, WiFi, or the like. A suitable reader, optionally employing a processor for taking further action based upon the signals, may provide the signals in a form suitable for interpretation by a user (e.g., by converting an electrical or optical signal into a pH value).

To correlate the change in the magnitude of the signal to an amount of analyte interacted with the sensing element, a user or a processor may utilize a lookup table, calibration curve, or the like. A lookup table may comprise comprising a plurality of analyte concentrations and a corresponding signal associated with those analyte concentrations. The lookup table may be populated before measuring an unknown sample by assaying multiple samples with known analyte concentrations, and determining the signal associated therewith. Optionally, a calibration curve or calibration function may be determined using the analyte concentration and signal data.

Embodiments disclosed herein include:

A. Affinity sensors. The affinity sensors comprise: at least one sensing element comprising a recognition moiety that interacts with an analyte by reversibly forming an analyte complex; wherein formation of the analyte complex is pH-dependent; and wherein the at least one sensing element provides a signal that changes when the analyte complex reversibly forms, and a change in magnitude of the signal is correlatable to an amount of analyte interacted with the at least one sensing element; and a solid-state pH-modulating element in proximity to the at least one sensing element.

B. Methods for regenerating an affinity sensor. The methods comprise: interacting an analyte with a sensing element comprising a recognition moiety that reversibly forms an analyte complex in a pH-dependent manner, the sensing element changing from a first state to a second state upon interacting with the analyte to form the analyte complex; wherein the sensing element provides a signal that changes when the analyte complex reversibly forms, and a change in magnitude of the signal between the first state and the second state is correlatable to an amount of analyte interacted with the sensing element; and actuating a solid-state pH-modulating element positioned in proximity to the sensing element.

Each of embodiments A and B may have one or more or all of the following additional elements in any combination:

Element 1: wherein the recognition moiety is a bio-based moiety or a biomimetic moiety.

Element 2: wherein the recognition moiety comprises at least one member selected from the group consisting of an antibody, a protein, a polypeptide, an aptamer, an affimer, a molecularly imprinted polymer, a glycopolymer, an oligonucleotide, and any combination thereof.

Element 3: wherein the signal is detectable optically, electrochemically, thermally, gravimetrically, calorimetrically, or any combination thereof.

Element 4: wherein the analyte and/or the recognition moiety undergoes protonation or deprotonation or a conformation change upon a pH change occurring in proximity to the at least one sensing element.

Element 5: wherein the solid-state pH-modulating element and the at least one sensing element are located upon an in-common substrate.

Element 6: wherein the solid-state pH-modulating element comprises a working electrode and at least one additional electrode.

Element 7: wherein the solid-state pH-modulating element comprises a material upon the working electrode that is operable to generate or consume protons when applying a potential or current thereto.

Element 8: wherein the material comprises at least one member selected from the group consisting of a metal hydride, a metal oxide, a metal hydroxide, polyaniline, a quinone-containing polymer, and any combination thereof.

Element 9: wherein the solid-state pH-modulating element comprises a Pd/PdH working electrode.

Element 10: wherein the affinity sensor further comprises a processor configured to determine a concentration of the analyte based upon the change in magnitude of the signal.

Element 11: wherein the solid-state pH-modulating element comprises a working electrode and at least one additional electrode, and actuating comprises applying a potential or current between the working electrode and the at least one additional electrode.

Element 12: wherein actuating the solid-state pH-modulating element changes pH at the sensing element and displaces the analyte from the analyte complex to convert the sensing element from the second state to the first state.

Element 13: wherein actuating the solid-state pH-modulating element changes pH at the sensing element to allow the analyte complex to form when interacting the analyte with the sensing element.

Element 14: wherein the solid-state pH-modulating element comprises a material upon the working electrode that is selected from the group consisting of a metal hydride, a metal oxide, a metal hydroxide, polyaniline, a quinone-containing polymer, and any combination thereof.

Element 15: wherein the method further comprises determining the change in magnitude of the signal; and correlating the change in magnitude of the signal to the amount of analyte that is interacted with the sensing element.

Element 16: wherein the method further comprises adjusting pH in a sample containing the analyte before interacting the analyte with the sensing element.

By way of non-limiting example, exemplary combinations applicable to A and/or B include, but are not limited to: 1 or 2, and 3; 1 or 2, and 4; 1 or 2, and 5; 1 or 2, and 6; 1 or 2, and 7; 1 or 2, and 7; 1 or 2, and 7; 1 or 2, and 10; 1 or 2, and 11; 1 or 2, and 12; 1 or 2, and 13; 1 or 2, and 14; 1 or 2, and 15; 1 or 2, and 16; 3 and 4; 3 and 5; 3 and 6; 3 and 7; 3 and 8; 3 and 9; 3 and 10; 3 and 11; 3 and 12; 3 and 13; 3 and 14; 3 and 15; 3 and 16; 4 and 5; 4 and 6; 4 and 7; 4 and 8; 4 and 9; 4 and 10; 4 and 11; 4 and 12; 4 and 13; 4 and 14; 4 and 15; 4 and 16; 5 and 6; 5 and 7; 5 and 8; 5 and 9; 5 and 10; 5 and 11; 5 and 12; 5 and 13; 5 and 14; 5 and 15; and 16; 6 and 7; 6 and 8; 6 and 9; 6 and 10; 6 and 11; 6 and 12; 6 and 13; 6 and 14; 6 and 15; 6 and 16; 7 and 8, and 9; 7 and 8, and 10; 7 and 8, and 11; 7 and 8, and 12; 7 and 8, and 13; 7 and 8, and 15; 7 and 8, and 16; 9 and 10; 9 and 11; 9 and 12; 9 and 13; 9 and 15; 9 and 16; 10 and 11; 10 and 12; 10 and 13; 10 and 14; 10 and 15; 10 and 16; 11, and 12 and/or 13; 11 and 14; 11 and 15; 11 and 16; 12 and/or 13, and 14; 12 and/or 13, and 15; 12 and/or 13 and 16; 14 and 15; 14 and 16; and 15 and 16.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. An affinity sensor comprising:
   at least one sensing element comprising a recognition moiety that interacts with an analyte by reversibly forming an analyte complex;
      wherein formation of the analyte complex is pH-dependent; and
      wherein the at least one sensing element provides a signal that changes when the analyte complex reversibly forms, and a change in magnitude of the signal is correlatable to an amount of analyte interacted with the at least one sensing element; and
   a working electrode and a counter electrode;
      wherein the working electrode is in proximity to the at least one sensing element; and
      wherein the working electrode has a material upon the working electrode that is operable to generate or consume protons when applying a potential or current thereto.

2. The affinity sensor of claim 1, wherein the recognition moiety is a bio-based moiety or a biomimetic moiety.

3. The affinity sensor of claim 2, wherein the recognition moiety comprises at least one member selected from the group consisting of an antibody, a protein, a polypeptide, an aptamer, an affimer, a molecularly imprinted polymer, a glycopolymer, an oligonucleotide, and any combination thereof.

4. The affinity sensor of claim 1, wherein the signal is detectable optically, electrochemically, thermally, gravimetrically, calorimetrically, or any combination thereof.

5. The affinity sensor of claim 1, wherein the analyte and/or the recognition moiety undergoes protonation or deprotonation or a conformation change upon a pH change occurring in proximity to the at least one sensing element.

6. The affinity sensor of claim 1, wherein the working electrode and the at least one sensing element are located upon an in-common substrate and wherein a separation between the working electrode and the at least one sensing element is 900 microns or less.

7. The affinity sensor of claim 1, wherein the material comprises at least one member selected from the group consisting of a metal hydride, a metal oxide, and any combination thereof.

8. The affinity sensor of claim 1, wherein the working electrode comprises a Pd/PdH working electrode.

9. A method comprising:
providing an affinity sensor comprising:
at least one sensing element comprising a recognition moiety that interacts with an analyte by reversibly forming an analyte complex;
wherein formation of the analyte complex is pH-dependent; and
wherein the at least one sensing element provides a signal that changes when the analyte complex reversibly forms, and a change in magnitude of the signal is correlatable to an amount of analyte interacted with the at least one sensing element; and
a solid state pH modulating element in proximity to the at least one sensing element;
a working electrode and a counter electrode;
wherein the working electrode is in proximity to the at least one sensing element; and
wherein the working electrode has a material upon the working electrode that is operable to generate or consume protons when applying a potential or current thereto; and
interacting an analyte with the sensing element comprising a recognition moiety that reversibly forms an analyte complex in a pH-dependent manner, the sensing element changing from a first state to a second state upon interacting with the analyte to form the analyte complex;
wherein the sensing element provides a signal that changes when the analyte complex reversibly forms, and a change in magnitude of the signal between the first state and the second state is correlatable to an amount of analyte interacted with the sensing element; and
actuating the working electrode.

10. The method of claim 9, wherein actuating the working electrode comprises applying a potential or current between the working electrode and the counter electrode.

11. The method of claim 10, wherein actuating the working electrode changes pH at the sensing element and displaces the analyte from the analyte complex to convert the sensing element from the second state to the first state.

12. The method of claim 10, wherein actuating the working electrode changes pH at the sensing element to allow that analyte complex to form when interacting the analyte with the sensing element.

13. The method of claim 10, wherein the material upon the working electrode is selected from the group consisting of a metal hydride, a metal oxide, polyaniline, a quinone-containing polymer, and any combination thereof.

14. The method of claim 10, wherein the working electrode is a Pd/PdH working electrode.

15. The method of claim 9, wherein the recognition moiety is a bio-based moiety or a biomimetic moiety.

16. The method of claim 15, wherein the recognition moiety comprises at least one member selected from the group consisting of an antibody, a protein, a polypeptide, an aptamer, an affimer, a molecularly imprinted polymer, a glycopolymer, an oligonucleotide, and any combination thereof.

17. The method of claim 9, further comprising:
determining the change in magnitude of the signal; and
correlating the change in magnitude of the signal to the amount of analyte that is interacted with the sensing element.

18. The method of claim 9, wherein the signal is detectable optically, electrochemically, thermally, gravimetrically, calorimetrically, or any combination thereof.

19. The method of claim 9, wherein the working electrode and the sensing element are located upon an in-common substrate.

20. The method of claim 9, further comprising:
adjusting pH in a sample containing the analyte before interacting the analyte with the sensing element.

21. The method of claim 9, wherein the analyte and/or the recognition moiety undergoes protonation or deprotonation or a conformation change upon a pH change occurring in proximity to the at least one sensing element.

* * * * *